United States Patent [19]

Peterson et al.

[11] Patent Number: 5,284,990
[45] Date of Patent: Feb. 8, 1994

[54] METHOD FOR CONVERTING A HYDROGEN FLUORIDE ALKYLATION UNIT TO A SULFURIC ACID ALKYLATION UNIT

[75] Inventors: Jon R. Peterson, Lee's Summit, Mo.; John B. Scott, San Rafael, Calif.

[73] Assignee: Stratco, Inc., Leawood, Kans.

[21] Appl. No.: 915,086

[22] Filed: Jul. 16, 1992

[51] Int. Cl.⁵ .......................... C07C 2/56; C07C 2/58; F28D 7/00
[52] U.S. Cl. .................................. 585/709; 585/718; 585/719; 585/720; 585/723; 585/730; 422/200; 422/235
[58] Field of Search .............. 585/709, 718, 719, 720, 585/723, 730; 422/200, 235

[56] References Cited

U.S. PATENT DOCUMENTS

| | | | |
|---|---|---|---|
| 4,018,846 | 4/1977 | Mayer | 585/730 |
| 4,225,740 | 9/1980 | Chapman et al. | 585/723 |
| 4,276,439 | 6/1981 | Hutson, Jr. et al. | 585/720 |
| 4,293,729 | 10/1981 | Kolb et al. | 585/730 |
| 4,371,731 | 2/1983 | Washer | 585/716 |
| 4,383,977 | 5/1983 | Hutson, Jr. et al. | 422/235 |
| 4,404,418 | 9/1983 | Hutson, Jr. et al. | 585/710 |
| 4,467,131 | 8/1984 | Washer et al. | 585/723 |
| 4,513,165 | 4/1985 | Van Pool | 585/723 |
| 4,777,323 | 10/1988 | Hann et al. | 585/719 |

OTHER PUBLICATIONS

Albright, Lyle F., Alkylation Will Be Key Process In Reformulated Gasoline Era, *Oil & Gas Journal*, Nov. 12, 1990, pp. 79-88.

Albright, Lyle F., H2SO4, HF Processes Copared, and New Technologies Revealed, *Oil & Gas Journal*, Nov. 26, 1990, pp. 70-77.

Chapin, L. E. and Masters, K. R., Conversion From HF to H2SO4 Alkylation: Incentives, Benefits, and Capital Considerations, presented at the 1988 National Petroleum Refiners Association Annual Meeting, Mar. 20-22, 1988, Convention Center, San Antonio, Texas.

Chapin, L. E., Liolios, G. C. and Robertson, T. M., Which Alkylation-HF or H2SO4?, reprinted from *Hydrocarbon Processing*, Sep. 1985 (pages unavailable).

C. R. Cupit, J. E. Gwyn & E. C. Jernigan, *Catalytic Alkylation*, a special report in two parts published in the Dec., 1961 and Jan., 1962 issues of Petro/Chem Engineer (pages unavailable).

*Primary Examiner*—Anthony McFarlane
*Assistant Examiner*—Nhat D. Phan
*Attorney, Agent, or Firm*—J. M. Gilbreth

[57] ABSTRACT

A method for converting HF alkylation unit to a sulfuric acid alkylation unit comprising the steps of retaining a reactor, an acid settler and a fractionation section from the HF alkylation unit and modifying at least a portion of the HF alkylation unit to produce a converted alkylation unit that is adapted to use sulfuric acid as a reaction catalyst.

21 Claims, 4 Drawing Sheets fig. 1.

METHOD FOR CONVERTING A HYDROGEN FLUORIDE ALKYLATION UNIT TO A SULFURIC ACID ALKYLATION UNIT

BACKGROUND OF THE INVENTION

The present invention relates to a method for converting a hydrogen fluoride alkylation unit to a sulfuric acid alkylation unit with a minimal amount of modification.

Sulfuric acid ($H_2SO_4$) and hydrogen fluoride (HF) have competed for many years for choice as the preferred alkylation catalyst for converting isobutane and light olefins to gasoline. Alkylation units adapted to use sulfuric acid as a reaction catalyst and alkylation units adapted to use HF as a reaction catalyst are currently in use. Both HF and sulfuric acid are hazardous materials. However, at ambient conditions, HF is a toxic, volatile gas while sulfuric acid is a toxic liquid, making sulfuric acid much easier to contain in the event of an accident. Refiners and citizens living near refineries are becoming more aware and concerned about the toxic and volatile nature of HF. Although extraordinary safety procedures are currently incorporated into HF alkylation units, recent incidents and testing show that HF aerosol releases past refinery boundaries are possible. Because of growing concerns over the hazardous nature of HF alkylation units, legislation has recently been approved which will effectively ban HF alkylation in certain parts of the United States.

In response to the growing concerns over HF alkylation, several refiners have added mitigation equipment to their HF alkylation units to minimize potential releases of HF outside the units. The primary mitigation equipment includes water sprays to "knock down" the HF aerosol before it leaves the refinery. Due to the large quantity of water needed to mitigate an HF release, such a mitigation system is costly. The installation of HF release mitigation systems may create a false sense of security. The accepted maximum effectiveness of HF release mitigation equipment is only 90%. The possibility of HF escaping the mitigation system is a real possibility. In addition, the HF release mitigation equipment installed in a refinery cannot protect against an HF release during unloading operations or from a rupture of trucks or railroad tank cars loaded with HF during transportation of HF to the refinery.

Due to the hazardous nature of HF, it would be desirable to be able to convert an alkylation unit adapted to use HF as the reaction catalyst to an alkylation unit adapted to use sulfuric acid as the reaction catalyst. However, due to differences in the properties of HF and sulfuric acid, as well as differences in HF and sulfuric acid alkylation reaction chemistry, sulfuric acid cannot simply be substituted for HF in an HF alkylation unit.

SUMMARY OF THE INVENTION

The present invention comprises a method for converting an HF alkylation unit adapted to use hydrogen fluoride as the reaction catalyst to a converted alkylation unit adapted to use sulfuric acid as the reaction catalyst. The method comprises the step of converting a portion of an HF alkylation unit while maintaining a portion of the HF alkylation unit intact. Prior to conversion, the HF alkylation unit generally comprises a hydrocarbon feed stream, an acid catalyst recycle stream, a reaction section, a settling section and a fractionation section. The hydrocarbon feed stream generally includes isobutane, light olefins ($C_3$ to $C_5$), propane and n-butane and the acid catalyst recycle stream comprises primarily hydrogen fluoride.

The hydrocarbon feed stream directs isobutane, light olefins, propane and n-butane to the reactor section and the acid catalyst recycle stream directs hydrogen fluoride to the reactor section. The unconverted HF alkylation unit further includes mixing or dispersing means such as spray nozzles for producing a degree of mixing necessary to form an HF reaction emulsion in the reaction section, the HF reaction emulsion having isobutane, light olefins and other hydrocarbons uniformly dispersed in hydrogen fluoride.

Emulsification of the isobutane, light olefins and hydrogen fluoride results in a hydrogen fluoride catalyzed alkylation reaction between isobutane and light olefins to produce alkylate in the HF reaction emulsion. The unconverted HF alkylation unit further comprises a cooling system for reducing the temperature of the HF reaction emulsion to approximately 80 to 110 degrees Fahrenheit.

The HF reaction emulsion is directed through the reactor section to the settling section comprising an acid settler wherein, during a settling period, the HF reaction emulsion separates into an HF acid phase comprising primarily hydrogen fluoride and a hydrocarbon phase comprising primarily alkylate ($C_5$ and heavier isoparaffins), isobutane, propane, n-butane and a small amount of hydrogen fluoride. The HF acid phase is recycled back to the reactor section through the acid catalyst recycle stream. The hydrocarbon phase is directed in an effluent stream to the fractionation section wherein the hydrocarbon phase is separated into a propane stream comprising primarily propane and hydrogen fluoride, an n-butane stream comprising primarily n-butane, an alkylate stream comprising primarily alkylate and an isobutane recycle stream comprising primarily isobutane which is recycled to the hydrocarbon feed stream. The propane stream and the n-butane stream each pass through a defluorinator and a KOH (potassium hydroxide) treater to remove isoalkyl fluorides and hydrogen fluoride from these streams.

The method includes the step of substituting sulfuric acid for hydrogen fluoride as the reaction catalyst. The method further includes the step of retaining the reactor section, the settling section and the fractionation section of the HF alkylation unit and modifying the HF alkylation unit to a sulfuric acid alkylation unit adapted to produce alkylate using sulfuric acid as the reaction catalyst. The step of modifying the HF alkylation unit includes modifying the mixing means to increase the degree of mixing to produce a sulfuric acid reaction emulsion having isobutane, light olefins and other hydrocarbons uniformly distributed in the sulfuric acid such that the isobutane and light olefins in the sulfuric acid reaction emulsion react to form alkylate.

The method further comprises the step of modifying the cooling system to cool the sulfuric acid reaction emulsion to approximately 20 to 70 degrees Fahrenheit; modifying the settling section to provide a longer settling period of approximately thirty minutes; and adding effluent treatment means to the effluent stream for removing acid esters and sulfuric acid from the effluent stream before fractionation.

The cooling system for the HF alkylation unit is modified such that the cooling system for the converted sulfuric acid alkylation unit is adapted to use a non-aqueous refrigerant such as propane, ammonia or freon as a refrigerant. The settling section is modified by adding an after settler to the HF alkylation unit such that in the converted sulfuric acid alkylation unit a top portion of the sulfuric acid reaction emulsion in the acid settler is directed to the after settler wherein the top portion separates into a hydrocarbon phase and a sulfuric acid phase.

OBJECTS AND ADVANTAGES OF THE INVENTION

Therefore, the principal objects of the present invention are: to provide a method for converting a hydrogen fluoride alkylation unit to a sulfuric acid alkylation unit comprising the steps of modifying at least a portion of the hydrogen fluoride alkylation unit and retaining at least a reactor, a settling section and a fractionation section of the hydrogen fluoride alkylation unit to produce a converted sulfuric alkylation unit that utilizes sulfuric acid as the reaction catalyst; to provide such a method that is relatively inexpensive when compared to constructing a sulfuric acid alkylation unit without using at least the reactor, the settling section and the fractionation section of the hydrogen fluoride alkylation unit; to provide such a method that is comparable in cost with adding to an HF alkylation unit equipment to minimize the effect of an accidental release of HF from the HF alkylation unit.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention comprises a method for converting an HF alkylation unit originally adapted to use hydrogen fluoride as the reaction catalyst to a converted alkylation unit subsequently adapted to use sulfuric acid as the reaction catalyst. In numbering the converted alkylation unit equipment that is incorporated from an HF alkylation unit (including modified equipment), the equipment for the converted alkylation unit will be labeled with the reference numeral for the corresponding unconverted HF alkylation unit equipment followed by the suffix b.

PHILLIPS HF ALKYLATION UNIT CONVERSION

Figure 1:
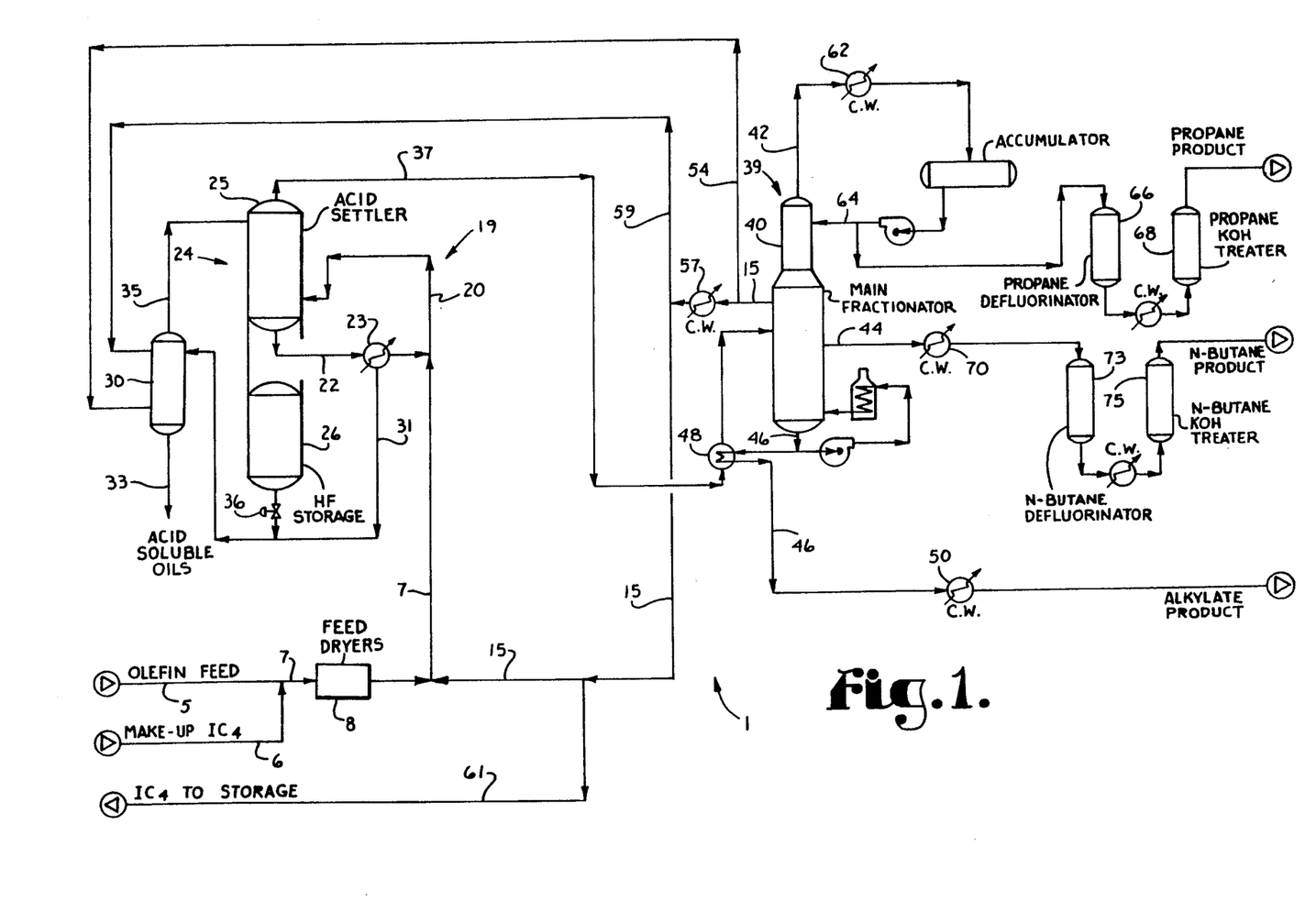
FIG. 1 is a schematic flow diagram of a Phillips HF alkylation unit, adapted to use HF as the reaction catalyst to produce alkylate.

FIG. 1 is a simplified flow diagram of an HF alkylation unit 1 designed and licensed by Phillips Petroleum Company (hereinafter referred to as a "Phillips HF alkylation unit"). The Phillips HF alkylation unit 1 is adapted to use hydrogen fluoride as the reaction catalyst to produce alkylate. Light olefins (olefins having three to five carbon atoms such as propylene, butylenes and amylene) in an olefin feed stream 5 and isobutane in a make-up isobutane feed stream 6 are mixed in a hydrocarbon feed stream 7. The hydrocarbon feed stream 7 then passes through feed dryers 8 to dry the light olefins and isobutane. Propane and n-butane are present in the olefin feed stream 5 but do not react with isobutane. The propane and n-butane act merely as diluents for the reaction. Additional isobutane is added to the hydrocarbon feed stream from a recycle isobutane stream 15.

The hydrocarbon feed stream 7 is directed to a reaction section 19 comprising a reactor 20. The reactor generally comprises a pipe which is typically about fifty feet long and sized for the unit's capacity. The reactor may also be referred to as a reactor pipe or a reactor riser. In the reactor 20 the light olefins and isobutane combine or mix with hydrogen fluoride from an acid catalyst recycle stream 22. Some mechanical mixing is generally provided to ensure thorough dispersion or mixing of isobutane and light olefins with the hydrogen fluoride to promote alkylation.

To provide the necessary mechanical mixing to uniformly disperse isobutane and light olefins in the hydrogen fluoride, the dried mixture of isobutane and light olefins is introduced into the reactor 20 through nozzles (not shown) at fairly high velocities. The injection of the light olefins and isobutane into the reactor 20 at fairly high velocities results in the formation of an HF reaction emulsion comprising isobutane and light olefins thoroughly distributed throughout the hydrogen fluoride. With hydrogen fluoride acting as a catalyst, the light olefins react with the isobutane in the HF reaction emulsion to produce alkylate.

Because the optimum reaction rate for hydrogen fluoride catalyzed alkylation occurs at temperatures on the order of 80° Fahrenheit (F.) to 110° F. the hydrogen fluoride in the acid catalyst recycle stream 22 is cooled prior to mixing with the light olefins and isobutane in the dry hydrocarbon feed stream 7. Cooling of the acid catalyst recycle stream 22 occurs in cooling means such as acid catalyst recycle cooler 23 which comprises a shell and tube heat exchanger. Hydrogen fluoride is passed through the shell side of the exchanger and cooling water is passed through the tube side of the exchanger to reduce the temperature of the hydrogen fluoride to approximately 80° to 110° F.

The HF reaction emulsion rises in the reactor 20 which is uncooled and enters a settling section 24 comprising an acid settler 25 wherein a hydrocarbon phase is allowed to separate from an HF acid phase of the HF reaction emulsion. The settling time necessary to allow separation of the HF acid phase from the hydrocarbon phase is relatively short, on the order of five minutes. The resulting hydrocarbon phase comprises mainly isobutane and alkylate with some propane, n-butane, dissolved hydrogen fluoride and isoalkyl fluorides. The HF acid phase comprises primarily hydrogen fluoride with some acid-soluble oils and water dissolved therein. The acid settler 25 is in a top section of a large two-section vertical column. Fresh liquid hydrogen fluoride is stored in a bottom section or HF storage drum 26 of the two-section vertical column.

Hydrogen fluoride in the HF acid phase continuously leaves the bottom of the acid settler 25 because of gravity and enters the acid catalyst recycle stream 22. As discussed above the acid catalyst recycle stream 22 is directed through the acid catalyst cooler 23 to remove the heat of reaction from the acid catalyst recycle stream 22 and reduce the temperature of the acid catalyst recycle stream 22 to approximately 80 to 110 degrees F.

A portion of the HF acid phase is separated from the acid catalyst recycle stream 22 out of the acid catalyst cooler 23 and directed to an HF regenerator 30 through HF slipstream 31. Acid-soluble oils present in the HF acid phase are stripped therefrom in the HF regenerator using isobutane as a stripper. The acid-soluble oils are removed from the bottom of the HF regenerator 30 in an acid-soluble oil stream 33. Hydrogen fluoride and isobutane are directed from the HF regenerator 30 back to the acid settler 25 through acid catalyst return stream 35. Fresh hydrogen fluoride may be introduced into the acid settler by opening valve 36 to the HF storage drum 26 to allow hydrogen fluoride to flow through HF slipstream 31, HF regenerator 30 and acid catalyst return stream 35 to the acid settler 25.

The hydrocarbon phase is drawn from the settler 25 through a hydrocarbon effluent stream 37 and is fed to a fractionation section 39 comprising a main fractionater 40. The main fractionater separates the hydrocarbon phase into four streams: an overhead or top stream 42 which comprises a mixture of hydrogen fluoride and propane; the recycle isobutane stream 15 which is mainly isobutane and which is recycled to the reactor 20 with the dry hydrocarbon feed stream 7; a vapor side stream 44 which comprises mainly n-butane; and a bottom stream 46 which comprises primarily alkylate. The hydrocarbon effluent stream 37 is heated prior to entry into the main fractionater 40 by passing the hydrocarbon phase in the hydrocarbon effluent stream 37 through the shell side of a feed/bottoms heat exchanger 48 and passing the bottom stream 46 through the tube side of the feed/bottoms heat exchanger 48. The alkylate in the bottom stream 46 is further cooled using an alkylate product cooler 50 which uses cooling water as a coolant.

A first portion of isobutane in the recycle isobutane stream 15 is diverted to the HF regenerator 30 through isobutane stripping stream 54. The isobutane in the isobutane stripping stream 54 is used to strip hydrogen fluoride from a mixture of hydrogen fluoride and acid-soluble oils in the HF regenerator 30. After the first portion of isobutane is removed from the recycle isobutane stream 15, the recycle isobutane stream 15 passes through a recycle isobutane cooler 57 which uses cooling water as a coolant to cool the recycle isobutane stream 15. After the isobutane in the recycle isobutane stream 15 is cooled in the recycle isobutane cooler 57, a second portion of isobutane is separated from the recycle isobutane stream 15 and directed to the HF regenerator 30 through isobutane reflux stream 59 to facilitate stripping of acid-soluble oils from the mixture of hydrogen fluoride and acid-soluble oils. A third portion of isobutane is separated from the recycle isobutane stream 15 and directed to storage through isobutane storage stream 61 which is optional.

An HF stripper (not shown) is provided to separate hydrogen fluoride from propane in the top stream 42. The top stream 42 is cooled in a propane condenser 62. A portion of the top stream 42 comprising primarily propane is directed back into the main fractionater 40 through propane reflux stream 64. The remainder of top stream 42 is directed through a propane defluorinator 66 and a propane KOH treater 68 to remove isoalkyl fluorides and hydrogen fluoride respectively.

The n-butane rich vapor side stream 44 is passed through a butane condenser 70 and then an n-butane defluorinator 73 to remove isoalkyl fluorides and an n-butane KOH treater 75 to remove hydrogen fluoride.

Figure 2:
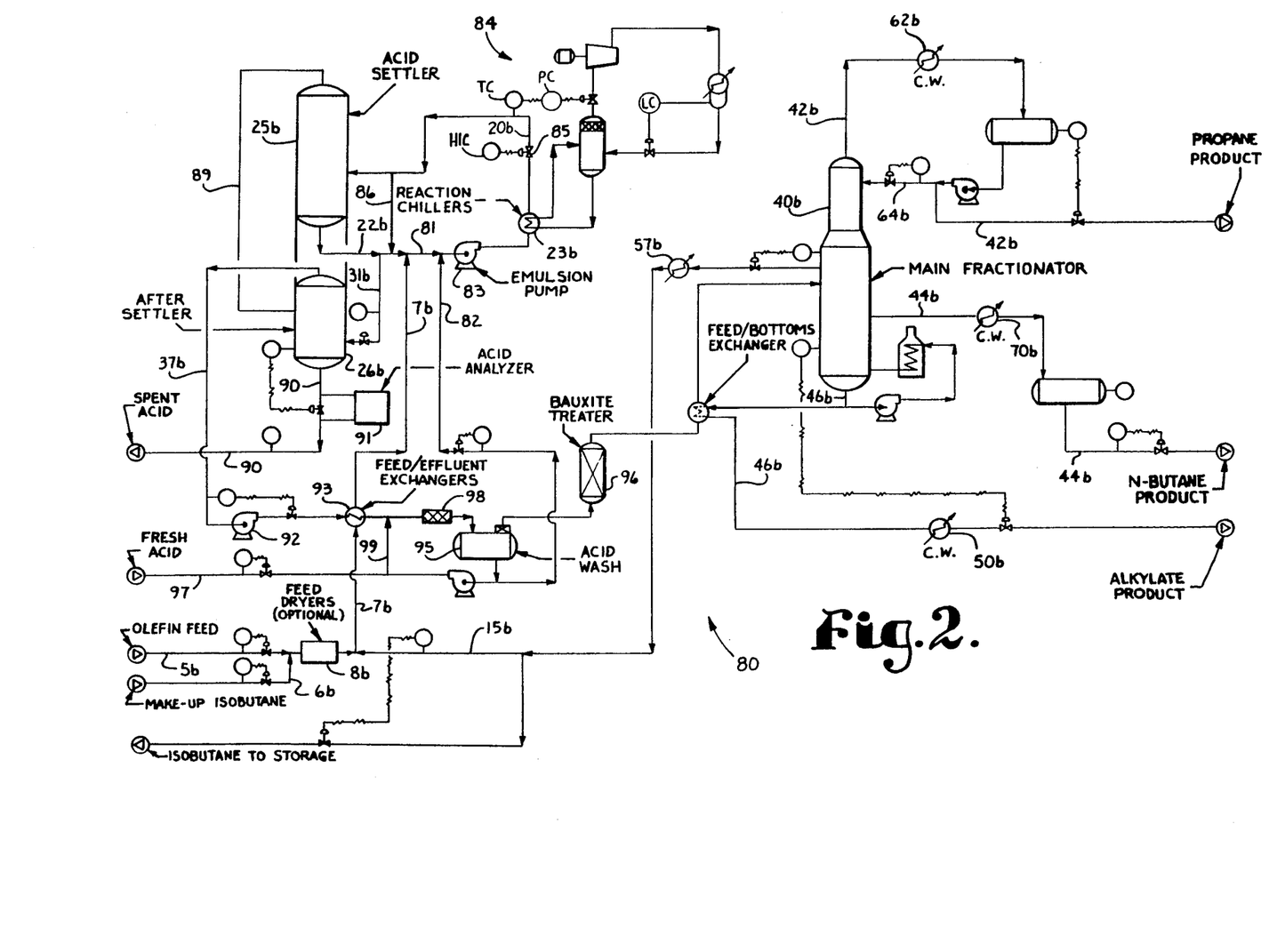
FIG. 2 is a schematic flow diagram of a converted Phillips HF alkylation unit, adapted to use sulfuric acid as the reaction catalyst.

FIG. 2 is a flow diagram of a Phillips HF alkylation unit 1 originally adapted to use hydrogen fluoride as a reaction catalyst that has been converted to a converted alkylation unit 80 adapted to use sulfuric acid as a reaction catalyst. Sulfuric acid is substituted for hydrogen fluoride as the reaction catalyst. The light olefin feed stream 5, the make-up isobutane stream 6, the dry hydrocarbon feed stream 7, the feed dryers 8 and the recycle isobutane stream 15 are reused in the converted alkylation unit 80 and become light olefin feed stream 5b, make-up isobutane stream 6b, dry hydrocarbon feed stream 7b, feed dryers 8b and recycle isobutane stream 15b. Light olefins from the olefin feed stream 5b and isobutane from the make-up isobutane feed stream 6b are mixed in the hydrocarbon feed stream 7b then passed through feed dryers 8b to dry the light olefins and isobutane. Additional isobutane is added to the hydrocarbon feed stream 7b from the recycle isobutane stream 15b downstream of the feed dryers 8b. The feed dryers 8b are optional in the converted alkylation unit 80.

The converted alkylation unit 80 further incorporates the reactor 20, the acid catalyst recycle stream 22 and the acid catalyst cooler 23 as reactor pipe 20b, acid catalyst recycle stream 22b and reaction chiller 23b respectively. The converted alkylation unit 80 also incorporates the acid settler 25 from the unconverted Phillips alkylation unit as initial acid settler 25b and the HF storage drum 26 as an after settler or secondary acid settler 26b. The hydrocarbon feed stream 7 from the unconverted Phillips alkylation unit is redirected such that the hydrocarbon feed stream 7b in the converted alkylation unit 80 intersects with the acid catalyst recycle stream 22b upstream of the reaction chiller 23b. The acid catalyst recycle stream 22b and the hydrocarbon feed stream 7b flow into a mixed reactant stream 81. The acid catalyst recycle stream 22b comprises primarily sulfuric acid. Relatively strong sulfuric acid is added to the mixed reactant stream 81 from a make-up sulfuric acid stream 82.

Sulfuric acid catalyzed alkylation requires that the isobutane and light olefins be thoroughly distributed throughout or mixed with the sulfuric acid to promote alkylation of isobutane and light olefins. If the isobutane and light olefins are not thoroughly distributed throughout the sulfuric acid, the light olefins will generally react with one another to form undesirable polymers. Because the viscosity of sulfuric acid is significantly greater than the viscosity of hydrogen fluoride, more mixing energy is required to thoroughly disperse isobutane and light olefins in sulfuric acid in the converted alkylation unit 80 than is provided by the HF alkylation unit 1 to disperse isobutane and light olefins in hydrogen fluoride.

To increase the mixing energy or degree of mixing, an emulsion pump 83 is added to the Phillips HF alkylation unit 1 such that the emulsion pump 83 is positioned upstream of the reaction chiller 23b. The mixed reactant stream 81 flows through the emulsion pump 83 such that the emulsion pump emulsifies or thoroughly disperses isobutane and light olefins throughout the sulfuric acid so as to form a sulfuric acid reaction emulsion. The isobutane and light olefins in the sulfuric acid reaction emulsion react to form alkylate. The hydrocarbon feed stream 7b preferrably intersects with the acid catalyst recycle stream 22b in close proximity to the emulsion pump 83 such that the isobutane, light olefins and sulfuric acid are emulsified almost immediately thereafter. Similarly, the make-up sulfuric acid stream 82 preferrably intersects with the mixed reactant stream 81 in close proximity to the emulsion pump 83.

From the emulsion pump 83, the sulfuric acid reaction emulsion in the mixed reactant stream 81 flows into the reaction chiller 23b. The reaction chiller 23b comprises one or more shell and tube heat exchangers which were originally used as the acid catalyst cooler 23 in the Phillips HF alkylation unit 1. Optimum reaction rates for sulfuric acid catalyzed alkylation in commercial applications typically occur at temperatures between 20° F. and 70° F. The acid catalyst cooler 23 is modified such that the resulting reaction chiller 23b is capable of cooling the reaction emulsion to the 20° F. to 70° F. range.

Due to the lower preferred reaction temperature for the sulfuric acid alkylation process as opposed to the HF alkylation process, cooling water cooling systems are generally inadequate for cooling the reactants of the sulfuric acid alkylation reaction to an optimum temperature range of from 20° F. to 70° F. Therefore, the acid catalyst cooler 23 of the Phillips alkylation unit is modified by replacing the tube bundle (not shown) of the acid catalyst cooler 23 with a tube bundle (not shown) adapted to use a non-aqueous refrigerant such as freon, ammonia, or propane in the reaction chiller 23b. Due to environmental concerns with the use of freon and ammonia and due to the relative availability of propane in a refinery, the preferred refrigerant for use in the reaction chiller 23b is propane.

A closed-loop propane refrigeration section 84 is added to the Phillips HF alkylation unit 1 and flow connected to the tube bundle of the reaction chiller 23b such that propane refrigerant is flashed on the tube side of the reaction chiller 23b. The reaction emulsion flows through the shell side of the reaction chiller 23b. Segmented baffles(not shown) or "egg crate type tube supports are to be added to the tube bundle of the reaction chiller 23b to increase the pressure drop and turbulence in the reaction chiller 23b to further emulsify the isobutane with the sulfuric acid phase. The reaction emulsion flows from the reaction chiller 23b through the reaction pipe 20b and into the acid settler 25b. Further mixing or emulsification may be provided by a mix valve 85 or a static mixer (not shown) or both which may be added to the reaction pipe 20b.

A significant portion of the alkylation reactions between isobutane and light olefins in the sulfuric acid reaction emulsion occur in the reaction chiller 23b. However, alkylation reactions foreseeably continue to occur throughout the reaction pipe 20b and in the acid settler 25b. The sulfuric acid reaction emulsion entering the acid settler 25b generally comprises sulfuric acid, alkylate, unreacted isobutane, propane, n-butane and acid esters which are an intermediate reaction product of the sulfuric acid catalyzed alkylation reactions.

Complete phase separation of a hydrocarbon phase from a sulfuric acid phase of the sulfuric acid reaction emulsion in a sulfuric acid alkylation process requires a settling time of approximately thirty minutes or longer, whereas complete phase separation of the reaction emulsion in an HF alkylation process requires approximately five minutes. In order to limit HF inventory in Phillips HF alkylation units, the acid settlers 25 of most Phillips HF alkylation units are sized to provide approximately five minutes of settling time and not much more. These acid settlers 25 are too small to provide adequate settling time to allow the sulfuric acid reaction emulsion to separate into the hydrocarbon phase and the sulfuric acid phase in the acid settler 25b of the converted alkylation unit 80. To promote increased separation of the reaction emulsion in the acid settler 25b, a first portion of the sulfuric acid reaction emulsion is drawn from the reaction pipe 20b and directed to the acid catalyst recycle stream 22b upstream of the mixed reactant stream 81 in a reaction emulsion recycle stream 86 (added to the Phillips HF alkylation unit 1) such that the first portion of the sulfuric acid reaction emulsion bypasses the acid settler 25b and is recycled back to the emulsion pump 83. Recycling the first portion of the sulfuric acid reaction emulsion to the emulsion pump 83 reduces the flow of sulfuric acid reaction emulsion into the acid settler 25b and increases the settling time available. Any internal components in the acid settler 25 from the unconverted Phillips HF alkylation unit 1 are removed from the acid settler 25b to reduce turbulence and to promote settling.

The sulfuric acid in the sulfuric acid reaction emulsion in the acid settler 25 does begin to settle towards the bottom of the acid settler 25b such that a bottom portion of the sulfuric acid reaction emulsion in the acid settler 25b has a higher concentration of sulfuric acid and a lower concentration of isobutane, alkylate, propane, and n-butane than a top portion of the sulfuric acid reaction emulsion in the acid settler 25b.

The sulfuric acid in the bottom portion is recycled to the emulsion pump 83 through the acid catalyst recycle stream 22b. A settler connect stream 89 is added to the Phillips HF alkylation unit 1 such that the lighter top portion of the sulfuric acid reaction emulsion in the acid settler 25b flows from the top of the acid settler 25b through the settler connect stream 89 to the HF storage drum 26 that has been converted to after settler 26b. The after settler 26b allows greater settling time for the sulfuric acid reaction emulsion. In the after settler 26b, the top portion of the sulfuric acid reaction emulsion from the acid settler 25b separates into a sulfuric acid phase comprising primarily sulfuric acid and a hydrocarbon phase comprising primarily alkylate, isobutane, propane, n-butane, some sulfuric acid and some acid esters. The sulfuric acid phase settles to the bottom of the after settler 26b and is discharged from the after settler 26b through a spent acid stream 90 added to the Phillips HF alkylation unit 1. An acid analyzer 91 is added to the spent acid stream 90 to monitor the strength of the sulfuric acid in the spent acid stream 90 and to regulate the flow of fresh acid makeup.

The acid catalyst slip stream 31 from the Phillips HF alkylation unit 1 is rerouted to form acid catalyst slip stream 31b. Acid catalyst slip stream 31b extends from the acid catalyst recycle stream upstream from where the sulfuric acid reaction emulsion recycle stream 86 intersects the acid catalyst recycle stream 22b which is upstream of reaction chiller 23b. The acid catalyst slip stream 31b is rerouted to flow connect with after settler 26b such that a portion of the sulfuric acid flowing through the acid catalyst recycle stream 22b is directed to the after settler 26b through acid catalyst slip stream 31b.

Hydrocarbon effluent stream 37 from the Phillips HF alkylation unit 1 is rerouted to connect with a top portion of after settler 26b so as to form hydrocarbon effluent stream 37b. The hydrocarbon phase in the after settler 26b flows out the top of the after settler 26b and into hydrocarbon effluent stream 37b.

An effluent pump 92 and a feed/effluent heat exchanger 93 are added to the Phillips HF alkylation unit 1 such that the hydrocarbon effluent stream 37b flows through the effluent pump 92 such that the contents of the hydrocarbon effluent stream 37b are pumped through the tube side of the feed/effluent heat exchanger 93.

The hydrocarbon feed stream 7b is directed through the shell side of the feed/effluent heat exchanger 93 such that the hydrocarbon effluent stream 37b cools the warm olefin and isobutane in the hydrocarbon feed stream 7b. Reducing the temperature of the hydrocarbon feed stream 7b using the feed/effluent heat exchanger 93 reduces the required refrigeration load on the refrigeration section 84.

The hydrocarbon effluent stream 37b in the converted alkylation unit 80 does contain corrosive sulfuric acid esters that are not present in a hydrogen fluoride catalyzed alkylation unit. Therefore, an effluent treating system is added to the Phillips HF alkylation unit 1 to remove the corrosive acid esters. The effluent treating system generally comprises acid wash drum 95 and a bauxite treater 96 or an optional hot alkaline water wash which is not shown. The acid wash drum 95 and bauxite treater 96 are installed in the converted alkylation unit 80 such that the hydrocarbon effluent stream 37b flows into the acid wash drum 95 which is positioned downstream from the feed effluent exchanger 93. Fresh acid at 98.5 weight percent sulfuric acid in a fresh acid stream 97 is mixed with the hydrocarbon phase in the hydrocarbon effluent stream 37b in a static mixer 98 positioned on the hydrocarbon effluent stream 37b between the feed/effluent heat exchanger 93 and the acid wash drum 95. The fresh acid removes the acid esters from the hydrocarbons in the hydrocarbon effluent stream 37b. The sulfuric acid and acid esters are then separated from the hydrocarbons using an electrostatic precipitator(not shown) in the acid wash drum 95. The acid flows out the bottom of the acid wash drum 95 and is separated into an acid wash recycle stream 99 and the make-up sulfuric acid stream 82. The acid wash recycle stream 99 is recycled back to hydrocarbon effluent stream 37b. The make-up sulfuric acid stream 82 is directed to the mixed reactant stream 81.

The hydrocarbon effluent stream 37b having acid esters removed therefrom flows out the top of the acid wash drum 95 and into the bauxite treater 96 or optional hot alkaline water wash where remaining neutral acid esters are removed therefrom. The hydrocarbon effluent stream 37b then flows to the main fractionater 40 from the Phillips HF alkylation unit 1 which is designated as 40b for the converted alkylation unit 80. No new equipment is added downstream of the main fractionater 40 of the Phillips HF alkylation unit 1 to convert it to the converted alkylation unit 80 adapted to use sulfuric acid as a reaction catalyst.

The hydrocarbon effluent stream 37b flows into the main fractionater 40b and is separated into top stream 42b which comprises primarily propane; the recycle isobutane stream 15b which comprises primarily isobutane, vapor side stream 44b which primarily comprises n-butane and bottom stream 46b which primarily comprises alkylate. The bottom stream 46b passes through the tube side of feed/bottoms heat exchanger 48b while the hydrocarbon effluent stream 37b passes through the shell side such that the bottom stream 46b preheats the hydrocarbon effluent stream 37b prior to entry into the main fractionater 40b. The alkylate in the bottom stream 46b is further cooled by alkylate product cooler 50b.

The isobutane stripping stream 54 and the isobutane reflux stream 59 from the Phillips HF alkylation unit 1 are removed but the recycle isobutane stream 15b does pass through recycle isobutane cooler 57b to reduce the temperature of the isobutane therein. The propane in the top stream 42b is cooled in propane condenser 62b and a portion of the propane in the top stream 42b is recycled back to the main fractionater 40b in the propane reflux stream 64b. Both the propane defluorinator 66 and the propane KOH treater 68 are removed from service.

The butane in the vapor side stream 44b is passed through butane condenser 70b. However, the n-butane defluorinator 73 and the n-butane KOH treater 75 are removed from service.

It is foreseeable that the n-butane KOH treater 75 or the propane KOH treater 68 or both could be reused as the bauxite treater 96.

UOP HF ALKYLATION UNIT CONVERSION

Figure 3:
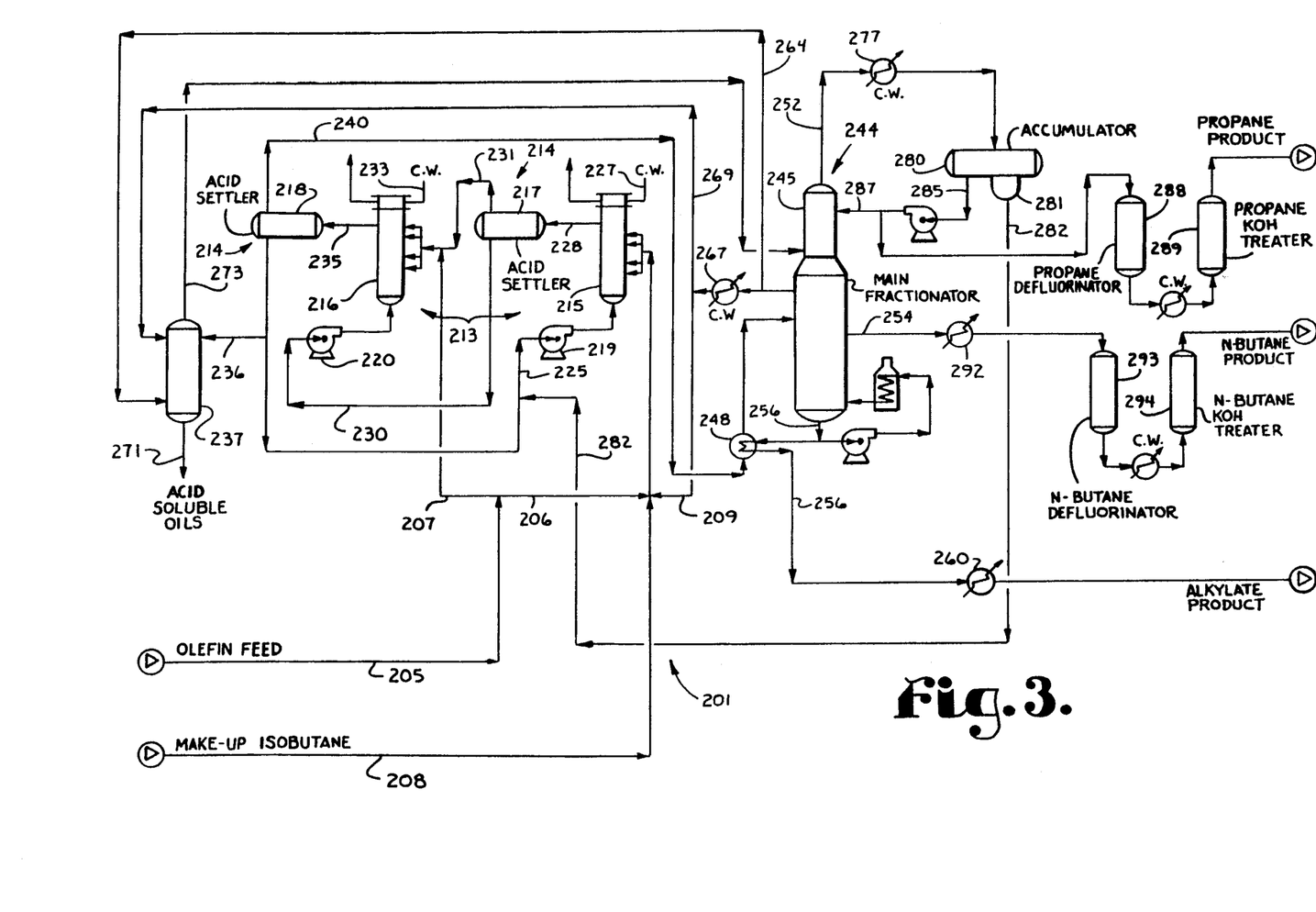
FIG. 3 is a schematic flow diagram of an UOP HF alkylation unit, adapted to use HF as the reaction catalyst to produce alkylate.

FIG. 3 is a simplified flow diagram of a UOP HF alkylation unit 201, adapted to use hydrogen fluoride as a reaction catalyst to produce alkylate. An olefin feed stream 205 containing light olefins, propane and n-butane is split into a first reactor hydrocarbon feed stream 206 and a second reactor hydrocarbon feed stream 207. Isobutane from a make-up isobutane feed stream 208 and a recycle isobutane stream 209 is mixed with the first reactor hydrocarbon feed stream 206.

The UOP HF alkylation unit 201 includes a reaction section 213 and a settling section 214. The reaction section 213 comprises a first reactor 215 and a second reactor 216. The settling section 214 comprises a first acid settler 217 and a second acid settler 218. The UOP HF alkylation unit 201 further comprises a first acid pump 219 and a second acid pump 220. The first reactor 215 and the second reactor 216 generally comprise vertically aligned tube and shell heat exchangers. It is foreseen that the heat exchangers may also be aligned horizontally or in other alignments. Hydrogen fluoride is introduced into the bottom of the shell side of the first reactor 215 from a first acid catalyst recycle stream 225 and light olefins, isobutane, propane and n-butane in the first reactor hydrocarbon feed stream 206 are introduced into the shell of the first reactor 215 through several nozzles (not shown) positioned at various heights in the shell. These nozzles cause the first reactor hydrocarbon feed stream 206 to be jetted into the hydrogen fluoride in the first reactor 215 to promote mixing and to form an HF reaction emulsion. The HF reaction emulsion generally comprises isobutane and light olefins uniformly dispersed throughout the hydrogen fluoride.

The HF reaction emulsion is maintained at a preferred temperature of approximately 80° to 110° F. by passing cooling water, in a first reactor cooling stream 227 through the tube side of the tube and shell heat exchanger which functions as cooling means. In the first reactor 215, the light olefins react with the isobutane in the presence of hydrogen fluoride in the HF reaction emulsion to produce alkylate.

The HF reaction emulsion from the first reactor 215 is transferred to the first acid settler 217 through first reactor effluent stream 228. In the first acid settler 217 the HF reaction emulsion is allowed to separate into a hydrocarbon phase (comprising primarily alkylate, isobutane, propane and n-butane) and an HF acid phase (comprising primarily hydrogen fluoride). The HF acid phase flows from the bottom of the first acid settler 217 through a second acid catalyst recycle stream 230 and into the bottom of the second reactor 216 on the shell side. The hydrocarbon phase from the first acid settler 217 flows from the top of the first acid settler 217 through a first acid settler hydrocarbon effluent stream 231 into the second reactor hydrocarbon feed stream 207 such that the light olefins in the second reactor feed stream 207 mix with the isobutane, propane, n-butane and alkylate in the first acid settler hydrocarbon effluent stream 231. The light olefins, isobutane, propane, n-butane and alkylate in the second reactor feed stream 207 are then introduced into the shell of the second reactor 216 through several nozzles (not shown) positioned at various heights in the shell to form an HF reaction emulsion with the hydrogen fluoride in the second reactor 216. The HF reaction emulsion is maintained at a preferred temperature of approximately 80° to 110° F. by passing cooling water, in a second reactor cooling stream 233 through the tube side of the tube and shell heat exchanger. Again, with hydrogen fluoride acting as a catalyst, the isobutane and light olefins in the HF reaction emulsion in the second reactor 216 react to produce alkylate. Isoalkyl fluorides are produced as a by-product of the alkylation reactions in both the first reactor 215 and the second reactor 216.

The HF reaction emulsion from the second reactor 216 is directed to the second acid settler 218 through a second reactor effluent stream 235. In the second acid settler 218 the HF reaction emulsion separates into the HF acid phase comprising primarily hydrogen fluoride and the hydrocarbon phase comprising primarily alkylate, isobutane, propane and n-butane with some hydrogen fluoride and isoalkyl fluorides entrained therein. The HF acid phase from the second acid settler 218 flows from the bottom of the second acid settler 218 in the first acid catalyst recycle stream 225. A portion of the hydrogen fluoride in the first acid catalyst recycle stream 225 is drawn off in a hydrogen fluoride slip stream 236 and is directed to HF regenerator 237. The first acid catalyst recycle stream 225 is directed through the first acid pump 219 and into the first reactor 215 under pressure. The second acid catalyst recycle stream 230 is similarly directed through second acid pump 220 and directed into the second reactor 216 under pressure.

The hydrocarbon phase from the second acid settler 218 flows through a hydrocarbon effluent stream 240 to a fractionation section 244 comprising a main fractionator 245. The hydrocarbon effluent stream 240 passes through the shell side of a feed/bottom heat exchanger 248 to preheat the hydrocarbon phase in the hydrocarbon effluent stream 240 prior to entry into the main fractionator 245. The main fractionator 245 separates the hydrocarbon phase in the hydrocarbon effluent stream 240 into four streams: a top stream 252 which comprises a mixture of hydrogen fluoride and propane; the recycle isobutane stream 209 which comprises mainly isobutane and which is recycled to the first reactor 215 through the first reactor feed stream 206; a vapor side stream 254 which comprises primarily n-butane; and a bottom stream 256 which comprises primarily alkylate.

The bottom stream passes through the tube side of the feed/bottom heat exchanger 248 to preheat the hydrocarbon phase in the hydrocarbon effluent stream 240 prior to entry into the main fractionator 245. The alkylate in the bottom stream is further cooled using an alkylate product cooler 260 which uses cooling water as a coolant.

A first portion of isobutane in the recycle isobutane stream 209 is diverted to the HF regenerator 237 in isobutane stripping stream 264. The isobutane in the isobutane stripping stream 264 is used to strip hydrogen fluoride from a mixture of hydrogen fluoride and acid soluble oils in the HF regenerator 237. After the first portion of isobutane is removed from the recycle isobutane stream 209, the recycle isobutane stream 209 passes through a recycle isobutane cooler 267 which uses cooling water as a coolant to cool the recycle isobutane stream 209. After the isobutane in the recycle isobutane stream 209 is cooled in the recycle isobutane cooler 267, a second portion of isobutane is separated from the recycle isobutane stream 209 and directed to the HF regenerator 237 in isobutane reflux stream 269 to facilitate stripping of acid soluble oils from the mixture of hydrogen fluoride and acid soluble oils.

The HF regenerator 237 produces a top product comprising primarily hydrogen fluoride and isobutane and a bottom product comprising primarily acid soluble oils. The acid soluble oils are removed from the HF regenerator in an acid soluble oil stream 271. The hydrogen fluoride and isobutane in the top product in the HF regenerator 237 are directed to the main fractionator through a hydrogen fluoride overhead stream 273.

Separation means such as an HF stripper (not shown) is provided for separating the hydrogen fluoride from the propane in the top stream 252. FIG. 3 shows the top stream 252 flowing through a propane condenser 277 which uses cooling water to cool and condense the propane and hydrogen fluoride in the top stream 252. The cooled and condensed propane and hydrogen fluoride enter a propane accumulator 280 wherein the heavier hydrogen fluoride accumulates in a boot 281. The hydrogen fluoride accumulated in the boot 281 is drawn off through hydrogen fluoride return stream 282 and mixed with hydrogen fluoride in the first acid catalyst recycle stream 225. A propane overhead stream 285 comprising primarily propane flows from the propane accumulator 280. A portion of the propane overhead stream 285 is directed to the main fractionator 245 in a propane reflux stream 287. The remainder of the propane overhead stream 285 is directed through a propane defluorinator 288 and a propane KOH treater 289 to remove isoalkyl fluorides and hydrogen fluoride respectively.

The n-butane rich vapor side stream 254 is passed through a butane condenser 292 and then an n-butane defluorinator 293 and an n-butane KOH treater 294 to remove isoalkyl fluorides and hydrogen fluoride respectively.

In the UOP HF alkylation unit 201 shown in FIG. 3, isobutane and hydrogen fluoride flow through the first reactor 215 and the second reactor 216 in series while light olefins flow through the first reactor 215 and the second reactor 216 in parallel. Although FIG. 3 discloses an UOP HF alkylation unit 201 utilizing two reactors wherein isobutane flows therethrough in series and light olefins flow through the reactors in parallel, UOP HF alkylation units 201 using a single reactor are utilized in plants with a relatively small capacity. In addition, some units utilize two reactors wherein both the light olefins and the isobutane flow through the reactors in parallel.

When the purity of isobutane available for the make-up isobutane feed stream 208 is relatively poor, the isobutane in the make-up isobutane feed stream 208 is initially directed through the main fractionater 245 and then to the reactor section 213 through the recycle isobutane stream 209 rather than directly to the reactor section.

Figure 4:
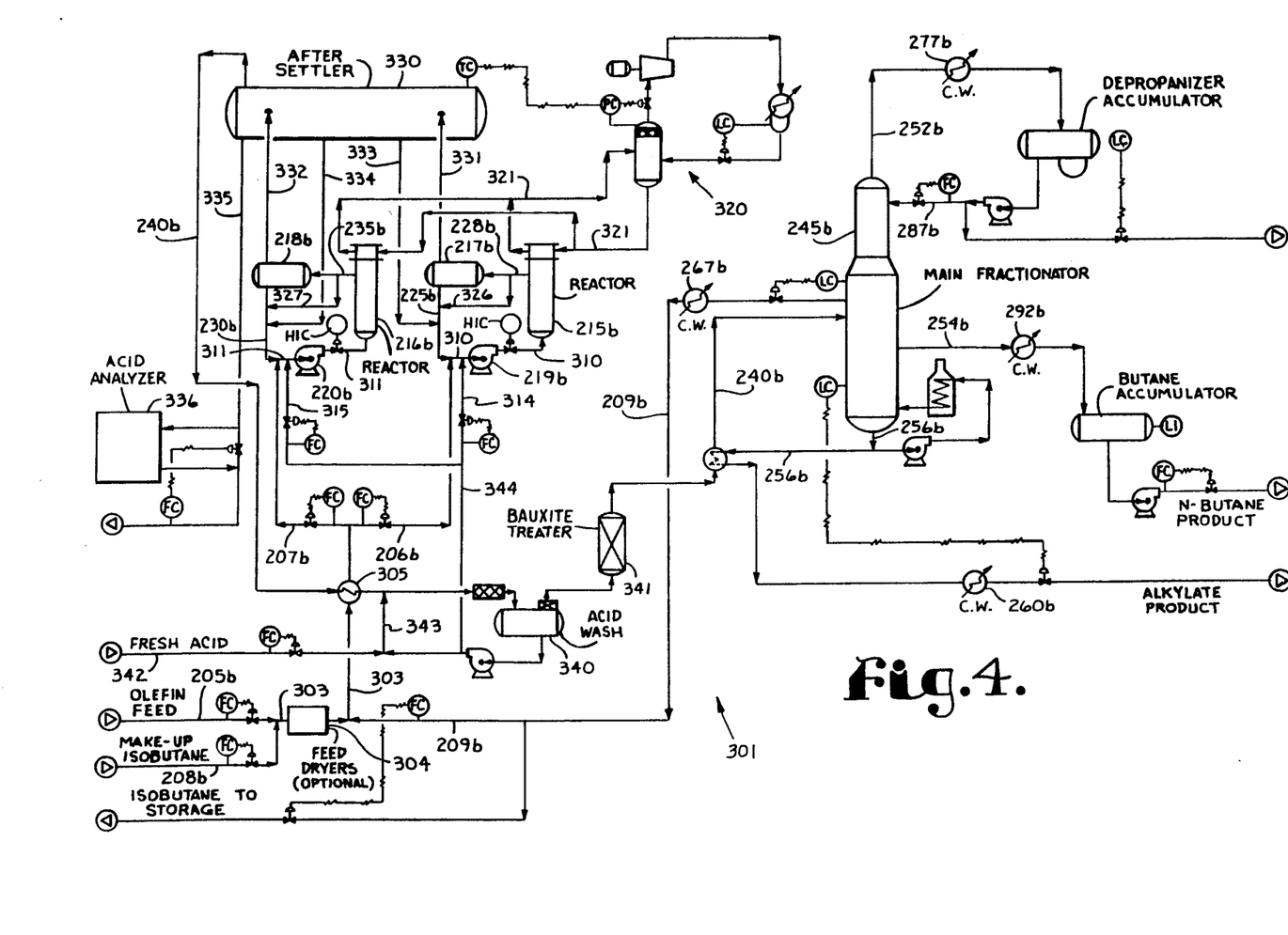
FIG. 4 is a schematic flow diagram of a converted UOP HF alkylation unit, adapted to use sulfuric acid as the reaction catalyst to produce alkylate.

FIG. 4 is a schematic flow diagram of a converted UOP HF alkylation unit 301 adapted to use sulfuric acid as a reaction catalyst. The method of conversion includes the step of substituting sulfuric acid for hydrogen fluoride as the reaction catalyst in the converted alkylation unit 301. The converted alkylation unit 301, as shown in FIG. 4, incorporates the olefin feed stream 205, the first reactor hydrocarbon feed stream 206, the second reactor hydrocarbon feed stream 207, the make-up isobutane feed stream 208 and the recycle isobutane stream 209 of the UOP HF alkylation unit 201 which become olefin feed stream 205b, first reactor hydrocarbon feed stream 206b, second reactor hydrocarbon feed stream 207b, make-up isobutane feed stream 208b and recycle isobutane stream 209b. Additionally, the converted alkylation unit 301, as shown in FIG. 4, includes a first reactor 215b, a second reactor 216b, a first acid settler 217b, a second acid settler 218b, a first emulsion pump 219b and a second emulsion pump 220b which generally correspond to the first reactor 215, the second reactor 216, the first acid settler 217, the second acid settler 218, the first acid settler 219 and the second acid pump 220 of the UOP HF alkylation unit 201, as shown in FIG. 3.

As shown in FIG. 4, the make-up isobutane feed stream 208 and the recycle isobutane stream 209 of the UOP HF alkylation unit 201 are rerouted in the converted alkylation unit 301 such that the make-up isobutane feed stream 208b joins the olefin feed stream 205b to form a hydrocarbon feed stream 303 which is dried in optional feed dryers 304, and the recycle isobutane stream 209b joins the hydrocarbon feed steam 303 after drying. The hydrocarbon feed stream 303 is then directed through the shell side of a feed/effluent heat exchanger 305 and then split into the first reactor hydrocarbon feed stream 206b and the second reactor hydrocarbon feed stream 207b.

Rerouting of the make-up isobutane feed stream 208 and the recycle isobutane stream 209 to join the olefin feed stream 205b and the hydrocarbon feed stream 303 prior to separation of the hydrocarbon feed stream 303 into the first reactor hydrocarbon feed stream 206b and the second reactor hydrocarbon feed stream 207b results in parallel flow of light olefins, isobutane and sulfuric acid through the first reactor 215b and second reactor 216b, whereas in the UOP HF alkylation unit 201, as shown in FIG. 3, the isobutane and hydrogen fluoride flow through the first reactor 215 and the second reactor 216 in series. It is foreseen that the converted alkylation unit 301 could be configured such that isobutane and sulfuric acid flow through the first reactor 215b and the second reactor 216b in series and the light olefins flow therethrough in parallel. It is also foreseeable that the converted alkylation unit 301 could be configured such that only sulfuric acid flowed through the first and second reactors 215b and 216b in series.

The first reactor hydrocarbon feed stream 206 and the second reactor hydrocarbon feed stream 207 are rerouted such that the first reactor hydrocarbon feed stream 206b and the second reactor hydrocarbon feed stream 207b join the first acid catalyst recycle stream 225b and the second acid catalyst recycle stream 226b respectively on the suction side of the first and second emulsion pumps 319b and 320b respectively. The first acid catalyst recycle stream 225b and the second acid catalyst recycle stream 226b correspond to the first acid catalyst recycle stream 225 and the second acid catalyst recycle stream 226 of the UOP HF alkylation unit 201. The first and second acid catalyst recycle streams 225b and 226b combine with the first and second reactor hydrocarbon feed streams 206b and 207b respectively to form a first mixed reactant stream 310 and a second mixed reactant stream 311. Additional sulfuric acid is added to the first and second mixed reactant streams 310 and 311 through a first make-up sulfuric acid stream 314 and a second make-up sulfuric acid stream 315 respectively.

Due to the differences in viscosity between sulfuric acid and hydrogen fluoride, the amount of mixing or emulsification provided by the UOP HF alkylation unit 201 would be inadequate to provide the degree of mixing or emulsification needed to thoroughly disperse isobutane and light olefins in sulfuric acid to promote alkylation. Therefore, the first emulsion pump 219b and the second emulsion pump 220b are substituted for the first acid pump 219 and the second acid pump 220. The first and second emulsion pumps 219b and 220b provide increased mixing capacity. In addition, the UOP HF alkylation unit 201 is modified such that in the converted alkylation unit 301 all of the reactants; isobutane and light olefins, as well as the acid catalyst; sulfuric acid, are passed through and mixed by either the first emulsion pump 219b or the second emulsion pump 220b.

More specifically, light olefins, isobutane and sulfuric acid are fed to the suction side of the first emulsion pump 219b and the second emulsion pump 220b through the first mixed reactant stream 310 and the second mixed reactant stream 311 respectively to thoroughly emulsify or distriute the isobutane and light olefins throughout the sulfuric acid so as to form a sulfuric acid reaction emulsion in the first and second mixed reactant streams 310 and 311 such that the isobutane contacts and reacts with the light olefins in the presence of sulfuric acid to produce alkylate in the sulfuric acid reaction emulsions. Acid esters are produced as a by-product of the sulfuric acid catalyzed alkylation reactions.

The first and second reactor hydrocarbon feed streams 206b and 207b preferrably intersect with the first and second acid catalyst recycle streams 225b and 226b in close proximity to the first and second emulsion pumps 219b and 220b respectively such that the isobutane, light olefins and sulfuric acid therein are emulsified almost immediately thereafter. Similarly, the first and second make-up sulfuric acid streams 314 and 315 preferrably intersect with the first and second mixed reactant streams 310 and 311 in close proximity to the first and second emulsion pumps 219b and 220b respectively.

The sulfuric acid reaction emulsions in the first mixed reactant stream 310 and the second mixed reactant stream 311 flow from the first emulsion pump 219b and the second emulsion pump 220b into the bottom of the first reactor 215b and the second reactor 216b respectively. A significant portion of the alkylation reactions occur in the first and second reactors 215b and 216b. The nozzles which were used to deliver hydrocarbons into the first reactor 215 and the second reactor 216 in the UOP HF alkylation unit 201 are plugged or removed from the first reactor 215b and second reactor 216b of the converted alkylation unit 301.

The first reactor 215b and the second reactor 216b in the converted alkylation unit 301 generally comprise the tube and shell heat exchangers from the UOP HF alkylation unit 201. The sulfuric acid reaction emulsions pass through the shell side of the first reactor 215b and the second reactor 216b and a coolant is passed through the tube bundle (not shown) in the first reactor 215b and the second reactor 216b.

The optimum reaction rates for sulfuric acid catalyzed alkylation reactions typically occur at temperatures ranging from 20° F. to 70° F., whereas the optimum reaction rates for hydrogen fluoride catalyzed alkylation reactions typically occur at temperatures ranging from approximately 80° F. to 110° F. Therefore, cooling water which is a suitable coolant for the UOP HF alkylation unit 201, as shown in FIG. 3, is not suitable for use in the converted alkylation unit 301 using sulfuric acid as a reaction catalyst. To provide the required cooling, a closed loop propane refrigeration section 320 is added to the UOP HF alkylation unit 201 and is flow connected to the tube bundles (not shown) of the first reactor 215b and the second reactor 216b to pass propane coolant therethrough. The tube bundles of the first reactor 215 and the second reactor 216 are modified for the first reactor 215b and the second reactor 216b such that the tube bundles are suitable for use with propane coolants. It is foreseen that other non-aqueous refrigerants such as freon or ammonia may be used in the tube bundles, however, due to environmental concerns over the use of freon and ammonia and due to the relative availability of propane in the refinery, propane is the preferred refrigerant. Propane is provided to the tube bundles through refrigerant stream 321 which runs in parallel through the tube bundles of the first reactor 215b and the second reactor 216b.

A first reactor effluent stream 228b and a second reactor effluent stream 235b corresponding to the first reactor effluent stream 228 and the second reactor effluent stream 235 in the UOP HF alkylation unit 201 carry the sulfuric acid reaction emulsions from the first reactor 215b and the second reactor 216b to the first acid settler 217b and the second acid settler 218b respectively. The first and second acid settlers 217b and 218b of most UOP HF alkylation units are too small to provide adequate settling time to allow a hydrocarbon phase to separate from a sulfuric acid phase in the sulfuric acid reaction emulsions. The sulfuric acid in the sulfuric acid reaction emulsions in the first acid settler 217b and the second acid settler 218b does begin to settle to the bottom of the first and second acid settlers 217b and 218b such that a bottom portion of the sulfuric acid reaction emulsions in the first and second acid settlers 217b and 218b comprises primarily sulfuric acid with lesser amounts of isobutane, alkylate, propane and n-butane and a top portion of the sulfuric acid reaction emulsion in the first and second acid settlers 217b and 218b comprises primarily alkylate, isobutane, propane and n-butane with lesser amounts of sulfuric acid and acid esters. However, in the first and second acid settlers 217b and 218b the sulfuric acid reaction emulsions typically do not separate into the sulfuric acid phase and the hydrocarbon phase.

Sulfuric acid in the bottom portion of the sulfuric acid reaction emulsions in the first and second acid settlers 217b and 218b is drawn off the bottom of the first acid settler 217b and the second acid settler 218b through the first acid catalyst recycle stream 225b and a second acid catalyst recycle stream 230b respectively. The second acid catalyst recycle stream 230b corresponds to the second acid catalyst recycle stream 230 of the UOP HF alkylation unit 201.

To provide increased settling time for the sulfuric acid reaction emulsions in the first and second acid settlers 217b and 218b, a portion of the sulfuric acid reaction emulsions in the first reactor effluent stream 228b and the second reactor effluent stream 235b are drawn off the first reactor effluent stream 228b and the second reactor effluent stream 235b through a first effluent slip stream 326 and a second effluent slip stream 327 and routed around the first acid settler 217b and the second acid settler 218b respectively and delivered to the first acid catalyst recycle stream 225b and the second acid catalyst recycle stream 230b respectively. By directing a portion of the sulfuric acid reaction emulsions from the first and second reactor effluent streams 228b and 235b around the first and second acid settlers 217b and 218b respectively, the volumetric flow rate of sulfuric acid reaction emulsion through the first and second acid settlers 217b and 218b is reduced thereby increasing the settling time available in the first and second acid settlers 217b and 218b.

Additional settling time for the sulfuric acid reaction emulsions in the converted alkylation unit 301 is provided by the addition of an after settler 330 to the UOP HF alkylation unit 201. The top portion of the sulfuric acid reaction emulsions from the first acid settler 217b and the second acid settler 218b is drawn from the top of the first acid settler 217b and the second acid settler 218b by a first settler connect stream 331 and a second settler connect stream 332 respectively and delivered to the after settler 330.

The hydrocarbon phase in the top portion or the sulfuric acid reaction emulsions drawn off the first acid settler 217b and the second acid settler 218b is allowed to separate from the sulfuric acid phase therein. A first portion of the sulfuric acid phase from the after settler 330 is drawn off the bottom of the acid settler 330 and recycled back to the first and second reactors 215b and 216b through a first acid return stream 333 and a second acid return stream 334 which join with the first acid catalyst recycle stream 225b and the second acid catalyst recycle stream 230b respectively. A second portion of the sulfuric acid phase in the acid settler 330 is drawn off in a spent acid stream 335 for regeneration. An acid analyzer 336 monitors the strength of the acid in the spent acid stream 335 to regulate the amount of acid withdrawn for regeneration.

The hydrocarbon effluent stream 240 from the UOP HF alkylation unit 201 is rerouted to form hydrocarbon effluent stream 240b which is flow connected to the after settler 330 and draws the hydrocarbon phase from the top of the after settler 330. The hydrocarbon effluent stream 240b comprises primarily alkylate, isobutane, n-butane and propane. The hydrocarbon effluent stream 240b is routed through the feed/effluent heat exchanger 305 through the tube bundle thereof to cool the light olefins and isobutane in the hydrocarbon feed stream 303.

The sulfuric acid catalyzed alkylation reaction produces corrosive acid esters in the hydrocarbon effluent stream 240b that are not present in a hydrogen fluoride alkylation unit. Therefore, an effluent treating system is added to the UOP HF alkylation unit 201 to remove the corrosive acid esters in the converted alkylation unit 301. The effluent treating system generally comprises an acid wash drum 340 and a bauxite treater 341 or an optional hot alkaline water wash which is not shown. The acid wash drum 340 and bauxite treater 341 are installed in the converted alkylation unit 301 such that the hydrocarbon effluent stream 240b flows into the acid wash drum 340 which is positioned downstream from the feed/effluent heat exchanger 305. Fresh acid at 98.5 percent by weight sulfuric acid in a fresh acid stream 342 is mixed with the hydrocarbon phase in the hydrocarbon effluent stream 240b between the feed effluent heat exchanger 305 and the acid wash drum 340. The fresh acid removes the acid esters from the hydrocarbon effluent stream 240b.

The sulfuric acid is then separated from the hydrocarbon effluent stream 240b using an electrostatic precipitator(not shown) in the acid wash drum 340. The acid flows out the bottom of the acid wash drum 340 and is separated into an acid wash recycle stream 343 and a make-up sulfuric acid stream 344 which is then separated into the first make-up sulfuric acid stream 314 and the second make-up sulfuric acid stream 315. The acid wash recycle stream 343 is recycled back to the fresh acid stream 342 and the hydrocarbon effluent stream 240b.

The first and second make-up sulfuric acid streams 314 and 315 are directed to the first and second mixed reactant streams 310 and 311 respectively. The hydrocarbon effluent stream 240b having acid esters removed therefrom flows out the top of the acid wash drum 340 and into the bauxite treater 341 or the optional hot alkaline water wash where remaining neutral esters are removed from the hydrocarbon effluent stream 240b. The hydrocarbon effluent stream 240b then flows to the main fractionator 245b which is incorporated from the main fractionator 245 in the UOP HF alkylation unit 201. No new equipment is added downstream of the main fractionator 245 of the UOP HF alkylation unit 201 to convert it to use sulfuric acid as a reaction catalyst.

The effluent in the hydrocarbon effluent stream 240b flows into the main fractionator 245b and is separated into: a top stream 252b which comprises primarily propane; the recycle isobutane stream 209b which comprises primarily isobutane; a side stream 254b which primarily comprises n-butane and a bottom stream 256b which primarily comprises alkylate. The bottom stream 256b passes through the tube side of the feed/bottom heat exchanger 248b while the hydrocarbon effluent stream 240b passes through the shell side such that the alkylate in the bottom stream 256b preheats the hydrocarbon effluent stream 240b prior to its entry into the main fractionator 245b. The alkylate in the bottom stream 256b is further cooled by the alkylate product isobutane reflux stream 269 from the UOP HF alkylation unit 201 are removed but the recycle isobutane stream 209b does pass through the recycle isobutane cooler 267b to reduce the temperature of the isobutane therein. The propane in the top stream 252b is cooled in the propane condenser 277b and a portion of the propane in the top stream 252b is recycled back to the main fractionator 245b in the propane reflux stream 287b. Both the propane defluorinator 288 and the propane KOH treater 289 of the UOP HF alkylation unit 201 are removed from service.

The n-butane in the side stream 254b is passed through the butane condenser 292b. However, the n-butane defluorinator 293 and the n-butane KOH treater 294 of the UOP HF alkylation unit 201 are removed from service.

It is foreseeable that the n-butane KOH treater 294 or the propane KOH treater 289 or both could be reused as the bauxite treater 341.

When alkylating light olefins with isobutane, it is necessary to have substantial excess isobutane in the reaction section. The presence of excess isobutane promotes the desired alkylation reactions while suppressing undesired polymerization reactions. The kinetics of the alkylation reactions with different catalysts at different temperatures indicate that the optimum external isobutane/olefin (I/O) ratio is in the range of 11–13 to 1 for HF alkylation and 7–9 to 1 for sulfuric acid alkylation. Based on these I/O ratios, the fractionation requirements would be greater in the case of HF alkylation. Therefore, the fractionation sections 39 and 244 of the HF alkylation units 1 and 201 would adequately sized for use in the converted alkylation units 80 and 301.

Both the unconverted Phillips HF alkylation units 1 and the unconverted UOP HF alkylation units 201 are typically constructed of carbon steel with the alloy sold under the trademark Monel being used in areas of high flow rates or turbulence such as pump impellers. In areas of relatively low flow rate and low turbulence the hydrogen fluoride reacts with the carbon steel to form an iron fluoride film that prevents further corrosion. In areas of high flowrate or turbulence, the high velocities or turbulence of the liquids continually wears away the film causing further corrosion.

Sulfuric acid can corrode Monel alloy. Therefore, in the converted HF alkylation units 80 and 301, any equipment made of Monel alloy that is in potential contact with sulfuric acid is replaced with equipment made of carbon steel, stainless steel or an alloy such as the alloy sold under the trademark Alloy 20. The sulfuric acid will react with carbon steel to form a corrosion resistant film of iron sulfate. However, in areas of high flow rates or high turbulence Alloy 20 alloy should be used because the high flow rates will tend to wear away the corrosion resistant film.

Before any of the equipment from the unconverted Phillips HF alkylation unit 1 or the unconverted UOP HF alkylation unit 201 that was in contact with hydrogen fluoride can be reused in the converted alkylation units 80 or 301 respectively, the corrosion resistant film of iron fluoride should be removed therefrom by means such as chemical cleaning which is well known in the art and relatively inexpensive.

It is to be understood that while certain forms of the present invention have been illustrated and described herein, it is not to be limited to the specific forms or arrangement of parts described and shown.

What is claimed and desired to be secured by Letters Patent is as follows:

1. A method for converting a hydrogen fluoride alkylation unit which utilizes hydrogen fluoride as a reaction catalyst to a sulfuric acid alkylation unit; said hydrogen fluoride alkylation unit comprising a reactor, a hydrocarbon feed stream directing isobutane and light olefins to the reactor and an acid catalyst stream directing the reaction catalyst to the reactor; mixing means for producing a degree of mixing necessary to form in said reactor an HF reaction emulsion comprising the isobutane and light olefins dispersed in the hydrogen fluoride wherein said isobutane reacts with said light olefins in the presence of hydrogen fluoride in said HF reaction emulsion to produce alkylate, a settling section having internals wherein, during a settling period, said HF reaction emulsion is separated into an HF acid phase and a hydrocarbon phase; and a fractionation section wherein alkylate in the hydrocarbon phase is separated therefrom; said method comprising the steps of:
   (a) substituting sulfuric acid for hydrogen fluoride as said reaction catalyst;
   (b) retaining said reactor, said settling section and said fractionation section; and
   (c) modifying said HF alkylation unit by adding increased mixing means for producing a degree of mixing necessary to form a sulfuric acid reaction emulsion comprising isobutane and light olefins dispersed in sulfuric acid wherein said isobutane reacts with said light olefins in the presence of sulfuric acid to produce alkylate.

2. The method as disclosed in claim 1 further comprising the steps of:
   (a) modifying said settling section of said HF alkylation unit to provide a longer settling period to allow said sulfuric acid reaction emulsion to separate into a sulfuric acid phase including sulfuric acid and a hydrocarbon phase including alkylate and isobutane, by removing the settling section internals and by routing a portion of the reaction emulsion back to the feed stream.

3. The method as disclosed in claim 2 wherein:
   (a) said increased mixing comprises an emulsion pump and said hydrocarbon feed stream and said acid catalyst recycle stream are redirected so as to intersect and form a mixed reactant stream on a suction side of said emulsion pump; said mixed reactant stream being directed through said emulsion pump and into said reactor.

4. The method as disclosed in claim 2 wherein:
   (a) said settling section of said HF alkylation unit comprises an acid settler and said settling section is modified by adding an after settler to said HF alkylation unit such that in said converted sulfuric acid alkylation unit a top portion of the sulfuric acid reaction emulsion in said acid settler is directed to said after settler wherein said top portion of said reaction emulsion separates into a sulfuric acid phase including sulfuric acid and a hydrocarbon phase including alkylate and isobutane and said hydrocarbon phase is removed from said after settler through an effluent stream.

5. The method as disclosed in claim 2 further comprising the step of:
   (c) modifying a cooling system of said HF alkylation unit which is adapted to use cooling water as a coolant to cool said HF reaction emulsion to a temperature range of approximately 80 to 110 degrees Fahrenheit such that said cooling system for said converted sulfuric acid alkylation unit is adapted to cool said sulfuric acid reaction emulsion to a temperature range of approximately 20 to 70 degrees Fahrenheit.

6. The method as disclosed in claim 2 wherein:
   (a) adding effluent treatment means to an effluent stream of said HF alkylation unit for removing acid esters and sulfuric acid from said effluent stream in said converted sulfuric acid alkylation unit; said effluent stream connecting said settling section to said fractionation section and directing said hydrocarbon phase from said settling section to said fractionation section.

7. A method for converting an HF alkylation unit adapted to use hydrogen fluoride as a reaction catalyst to a converted sulfuric acid alkylation unit adapted to use sulfuric acid as a reaction catalyst, said HF alkylation unit comprising a hydrocarbon feed stream directing isobutane and light olefins to a reactor section and an acid catalyst recycle stream directing hydrogen fluoride to said reactor section; said HF alkylation unit further including mixing means for producing a degree of mixing necessary to form an HF reaction emulsion in said reaction section comprising isobutane and light olefins dispersed in hydrogen fluoride to promote a hydrogen fluoride catalyzed alkylation reaction between isobutane and light olefins to produce alkylate; said HF alkylation unit further comprising cooling means for reducing the temperature of said reaction emulsion to a range of approximately 80 to 110 degrees Fahrenheit; said reaction emulsion being directed through said reactor section to a settling section having internals wherein, during a settling period, a hydrocarbon phase separates from an HF acid phase; said HF acid phase comprising primarily hydrogen fluoride and being recycled back to said reactor section through said acid catalyst recycle stream; said hydrocarbon phase being directed in an effluent stream to a fractionation section wherein an alkylate stream comprising primarily alkylate is separated from said hydrocarbon phase; the method comprising the steps of:
   (a) substituting sulfuric acid for hydrogen fluoride as said reaction catalyst;
   (b) increasing the degree of mixing to produce a sulfuric acid reaction emulsion having isobutane and light olefins uniformly dispersed in sulfuric acid; the isobutane and light olefins in said sulfuric acid reaction emulsion reacting to form alkylate;
   (c) modifying said cooling means to cool said reaction emulsion to a range of approximately 20 to 70 degrees Fahrenheit;
   (d) modifying said settling section, by removing the settling section internals and by routing a portion of the reaction emulsion back to the reactor section, to provide a longer settling period sufficient to allow said sulfuric acid reaction emulsion to separate into a hydrocarbon phase comprising alkylate and isobutane and a sulfuric acid phase comprising primarily sulfuric acid; and
   (e) adding effluent treatment means to said effluent stream for removing sulfuric acid from said effluent stream.

8. The method as disclosed in claim 7 wherein the hydrocarbon feed stream of the unconverted HF alkylation unit is injected into the reaction section through nozzles to promote mixing between the isobutane, the light olefins and the hydrogen fluoride; further comprising the steps of:

(a) rerouting said hydrocarbon feed stream to flow into said acid catalyst recycle stream upstream of said reaction section to form a mixed reactant stream; and (b) directing said mixed reactant stream through an emulsion pump and into said reaction section; said emulsion pump producing said sulfuric acid reaction emulsion.

9. The method as disclosed in claim 7 wherein said cooling means of said HF alkylation unit comprises a shell and tube heat exchanger having a tube bundle adapted to use cooling water as a coolant and said step of modifying said cooling means comprises:

(a) modifying said tube bundle to be adapted to use as a coolant a non-aqueous refrigerant.

10. The method as disclosed in claim 7 wherein the settling section of said HF alkylation unit comprises an acid settler; said method further comprising the steps of:

(a) adding an after settler;

(b) connecting said after settler to said acid settler such that a bottom portion of the sulfuric acid reaction emulsion in said acid settler is recycled to said reactor section through said acid catalyst recycle stream and a top portion of the sulfuric acid reaction emulsion in said acid settler is drawn from said acid settler to said after settler wherein said top portion is allowed to separate into said hydrocarbon phase and said sulfuric acid phase; and (c) rerouting said effluent stream to direct said hydrocarbon phase from said after settler to said main fractionator.

11. The method as disclosed in claim 7 further comprising the step of:

(a) adding a feed/effluent heat exchanger to said unit and directing said hydrocarbon feed stream and said effluent stream through said feed/effluent heat exchanger to cool said hydrocarbon feed stream and heat said effluent stream.

12. A method for converting an HF alkylation unit adapted to use hydrogen fluoride as a reaction catalyst to a converted sulfuric acid alkylation unit adapted to use sulfuric acid as a reaction catalyst, said HF alkylation unit comprising a hydrocarbon feed stream including a mixture of isobutane, light olefins, propane and n-butane; said hydrocarbon feed stream being directed to reactor wherein said hydrocarbon feed stream is mixed with hydrogen fluoride from an acid catalyst recycle stream; said acid catalyst recycle stream passing through an acid catalyst recycle cooler using cooling water as a coolant to cool said acid catalyst recycle stream to a range between approximately 80 and 110 degrees Fahrenheit prior to mixing with said hydrocarbon feed stream; said hydrocarbon feed stream being injected into said reactor through nozzles to promote mixing between the isobutane, light olefins and hydrogen fluoride so as to form an HF reaction emulsion having isobutane and light olefins dispersed in hydrogen fluoride; said isobutane reacting with said light olefins in said HF reaction emulsion to produce alkylate; said HF reaction emulsion being directed to an acid settler having internals wherein, during a settling period, a hydrocarbon phase separates from an HF acid phase of said HF reaction emulsion; said hydrocarbon phase comprising alkylate, isobutane, propane and n-butane and said HF acid phase comprising primarily hydrogen fluoride; a portion of said HF acid phase being recycled to said reactor in said acid catalyst recycle stream and said hydrocarbon phase being directed in an effluent stream to a fractionation section wherein said hydrocarbon phase in separated into an alkylate stream, said isobutane recycle stream, a propane stream and an n-butane stream; said isobutane recycle stream is directed to said hydrocarbon feed stream; said method of conversion comprising the steps of:

(a) substituting sulfuric acid for hydrogen fluoride as said reaction catalyst;

(b) adding an emulsion pump to said unit upstream of said acid catalyst recycle cooler and redirecting said hydrocarbon feed stream and said acid catalyst recycle stream such that said hydrocarbon feed stream and said acid catalyst recycle stream intersect on a suction side of said emulsion pump to form a mixed reactant stream that is directed through said emulsion pump and to said acid catalyst recycle cooler; said emulsion pump adapted to provide adequate mixing to form a sulfuric acid reaction emulsion comprising isobutane and light olefins dispersed in sulfuric acid; the isobutane reacting with the light olefins in the presence of sulfuric acid in the sulfuric acid reaction emulsion to produce alkylate;

(c) modifying said acid catalyst recycle cooler to form a reaction chiller adapted to use as a coolant a non-aqueous refrigerant adapted to reduce the temperature of the sulfuric acid reaction emulsion to within a range from approximately 20 to 70 degrees Fahrenheit; said sulfuric acid reaction emulsion being directed from said reaction chiller, through said reactor and into said acid settler;

(d) modifying the acid settler by removing the settler internals, by routing a portion of the reaction emulsion back to the reactor, and by adding an after settler such that a top portion of said sulfuric acid reaction emulsion from said acid settler is directed from said acid settler to said after settler wherein a hydrocarbon phase comprising primarily alkylate, isobutane, propane and n-butane separates from a sulfuric acid phase of said sulfuric acid reaction emulsion; said sulfuric acid phase comprising primarily sulfuric acid;

(e) redirecting said effluent stream to draw said hydrocarbon phase from said after settler and redirecting said effluent stream through a feed/effluent heat exchanger;

(f) directing said hydrocarbon feed stream through said feed/effluent heat exchanger such that said effluent stream cools said hydrocarbon feed stream;

(g) adding effluent treatment means to said effluent stream for removing acid esters and sulfuric acid from said effluent stream.

13. The method as disclosed in claim 12 comprising the further step of:

(a) adding baffles to said reaction chiller to increase the turbulence and pressure drop in said reaction chiller to further emulsify said sulfuric acid reaction emulsion.

14. The method as disclosed in claim 12 wherein said effluent treatment means comprises the steps of:

(a) mixing said effluent stream with strong sulfuric acid to remove acid esters from said effluent stream;

(b) separating said strong sulfuric acid from said effluent stream in an acid wash drum; and (c) directing said effluent stream through a hot alkaline water wash to remove any sulfuric acid from said effluent stream.

15. A method for converting an HF alkylation unit adapted to use hydrogen fluoride as a reaction catalyst to a converted sulfuric acid alkylation unit adapted to use sulfuric acid as a reaction catalyst, said HF alkylation unit comprising a hydrocarbon feed stream including a mixture of light olefins, propane, n-butane and isobutane, an acid catalyst recycle stream; comprising primarily hydrogen fluoride, an acid catalyst pump, a reactor, an acid settler having internals and a fractionator; said acid catalyst pump being positioned on said acid catalyst recycle stream and pumping hydrogen fluoride from said acid settler to said reactor; said hydrocarbon feed stream being directed to said reactor wherein said hydrocarbon feed stream is injected into said reactor through a plurality of nozzles so as to mix the light olefins, isobutane, propane, and n-butane in said hydrocarbon feed stream with the hydrogen fluoride from said acid catalyst recycle stream to form an HF reaction emulsion having isobutane and light olefins uniformly dispersed in hydrogen fluoride; said isobutane reacting with said light olefins in said HF reaction emulsion to produce alkylate; said reactor including a cooling coil using cooling water as a coolant for maintaining the temperature of the reaction emulsion in the reactor at approximately 80 to 110 degrees Fahrenheit; said reaction emulsion being directed to the acid settler wherein, during a settling period, a hydrocarbon phase including alkylate, isobutane, propane and n-butane separates from an HF acid phase of said HF reaction emulsion; said HF acid phase comprising primarily hydrogen fluoride; a portion of said HF acid phase being recycled to said reactor in said acid catalyst recycle stream and said hydrocarbon phase being directed in an effluent stream to a fractionation section wherein said hydrocarbon phase is separated into an alkylate stream, an isobutane recycle stream, a propane stream and an n-butane stream; said isobutane recycle stream being directed to said hydrocarbon feed stream; said method of conversion comprising the steps of:

(a) substituting sulfuric acid for hydrogen fluoride as said reaction catalyst (b) replacing said acid catalyst pump with an emulsion pump and redirecting said hydrocarbon fed stream such that said hydrocarbon feed stream and said acid catalyst recycle stream intersect on a suction side of said emulsion pump to form a mixed reactant stream that is directed through said emulsion pump and to said reactor; said emulsion pump adapted to provide adequate mixing to form a sulfuric acid reaction emulsion comprising isobutane and light olefins uniformly dispersed in sulfuric acid; the isobutane reacting with the light olefins in the presence of sulfuric acid in the sulfuric acid reaction emulsion to produce alkylate;

(c) modifying said cooling coil to use as a coolant a non-aqueous refrigerant such that said cooling coil is adapted to reduce the temperature of the sulfuric acid reaction emulsion in the reactor to approximately 20 to 70 degrees Fahrenheit;

(d) modifying the acid settler by removing settler internals, by routing a portion of the reactor emulsion back to the reactor, and by adding an after settler to said unit; said sulfuric acid reaction emulsion being directed from said reactor to said acid settler wherein a top portion of said sulfuric acid reaction emulsion is directed from said acid settler to said after settler wherein a hydrocarbon phase comprising primarily alkylate, isobutane, propane and n-butane is separated from a sulfuric acid phase of said sulfuric acid reaction emulsion; said sulfuric acid phase comprising primarily sulfuric acid;

(e) redirecting said effluent stream to draw said hydrocarbon phase from said after settler and redirecting said effluent stream through a feed/effluent heat exchanger;

(f) directing said hydrocarbon feed stream through said feed/effluent heat exchanger such that said effluent stream cools said hydrocarbon feed stream;

(g) adding effluent treatment means to said effluent stream for removing acid esters and sulfuric acid from said effluent stream.

16. The method as disclosed in claim 15 comprising the further step of:

(a) adding baffles to said reactor to increase the turbulence and pressure drop in said reactor to further emulsify said sulfuric acid reaction emulsion.

17. The method as disclosed in claim 15 wherein said effluent treatment means comprises the steps of:

(a) mixing said effluent stream with strong sulfuric acid to remove acid esters from said effluent stream;

(b) separating said strong sulfuric acid from said effluent stream in an acid wash drum; and (c) directing said effluent stream through a bauxite treater to remove any sulfuric acid from said effluent stream.

18. In a method for the conversion of an HF alkylation unit to an $H_2SO_4$ alkylation unit wherein the HF alkylation unit comprises an alkylation reactor having a reaction emulsion stream, and an HF acid settler having internal components to phase separate the reactor reaction emulsion stream, and wherein one step of the conversion method comprises complete replacement of the HF acid settler with an $H_2SO_4$ acid settler, the improvement in the method comprises conversion of the HF acid settler into a suitable $H_2SO_4$ settler by removing the internal components of the HF acid settler.

19. The method of claim 18 further comprising routing a portion of the reaction emulsion stream back to the alkylation reactor to increase the phase settling time of the converted acid settler.

20. In a method for the conversion of an HF alkylation unit to an $H_2SO_4$ alkylation unit wherein the HF alkylation unit comprises an alkylation reactor having a reaction emulsion stream, and an HF acid settler to phase separate the reactor reaction emulsion stream, and wherein one step of the conversion method comprises complete replacement of the HF acid settler with an $H_2SO_4$ acid settler, the improvement in the method comprises conversion of the HF acid settler into a suitable $H_2SO_4$ settler by routing a portion of the reaction emulsion stream back to the alkylation reactor to increase the phase settling time of the converted acid settler.

21. In a method for the conversion of an HF alkylation unit to an $H_2SO_4$ alkylation unit wherein the HF alkylation unit comprises an alkylation reactor having a reaction emulsion stream, an HF acid settler to phase separate the reaction emulsion stream into a hydrocarbon stream and an acid stream, and a heat exchanger having tube bundles adapted to use aqueous refrigerants to cool the acid stream for recycle back to the reactor, and wherein one step of the conversion method comprises replacement of heat exchanger, the improvement in the method comprises incorporating the heat exchanger into the reactor by replacing the tube bundle with a tube bundle adapted to use a non-aqueous refrigerant.

* * * * *